(12) United States Patent
Allen et al.

(10) Patent No.: US 6,660,909 B1
(45) Date of Patent: Dec. 9, 2003

(54) CYCLOPROPANE-FATTY-ACYL-PHOSPHOLIPID SYNTHASE

(75) Inventors: Stephen M. Allen, Wilmington, DE (US); Anthony J. Kinney, Wilmingtion, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 6 days.

(21) Appl. No.: 09/644,907

(22) Filed: Aug. 24, 2000

Related U.S. Application Data

(63) Continuation of application No. PCT/US99/03455, filed on Feb. 18, 1999.
(60) Provisional application No. 60/076,203, filed on Feb. 27, 1998.

(51) Int. Cl.[7] .......................... A01H 3/00; C07H 21/04; C07K 14/415; C12N 5/14; C12N 9/00
(52) U.S. Cl. ......................... 800/295; 435/6; 435/69.1; 435/410; 435/419; 435/252.3; 435/320.1; 435/183; 530/350; 530/370; 536/23.1; 536/23.6; 536/24.1; 800/278
(58) Field of Search .......................... 435/6, 69.1, 410, 435/419, 252.3, 320.1, 183; 530/350, 370; 536/23.1, 23.6, 24.1; 800/278, 295

(56) References Cited

U.S. PATENT DOCUMENTS 5,658,773 A * 8/1997 Bennett et al.

FOREIGN PATENT DOCUMENTS

| WO | 96/38581 | 12/1996 |
| WO | 99/18217 | 4/1999 |

OTHER PUBLICATIONS

Frederick R. Taylor et al., Methods in Enzymology, vol. 71:133–139, 1981, Cyclopropane Fatty Acid Synthase from *Escherichia coli*.
Dennis W. Grogan et al., Journ. of Bacteriology, vol. 158(1):286–295, Apr. 1984, Cloning and Manipulation of the *Escherichia coli* Cyclopropane Fatty Acid Synthase Gene: Physiological Aspects of Enzyme Overproduction.
Ying Yuan et al., PNAS, vol. 92:6630–6634, Jul. 1995, Identification of a gene involved in the biosynthesis of cyclopropanated mycolic acids in *Mycobacterium tuberculosis*.
Warren Gish et al., Nature genetics, vol. 3:266–272, Mar. 1993, Identification of Protein Coding Regions by Database Similarity Search.
National Center for Biotechnology Information General Identifier No. Z77162, Jun. 17, 1998.
S. T. Cole et al., Nature, vol. 393:537–544, 1998, Deciphering the Biology of *Mycobacterium tuberculosis* from the complete genome sequence.
National Center for Biotechnology Information General Identifier No. M98330, Apr. 26, 1993.
Ai–Yu Wang et al., Biochemstry, vol. 31:11020–11028, 1992, Cyclopropane Fatty Acid Synthase of *Eschericia coli* Deduced Amino Acid Sequence, Purification, and Studies of the Enzyme Active Site.
National Center for Biotechnology Information General Identifier No. Q1195, Dec. 15, 1998.
National Center for Biotechnology Information General Identifier No. 231731, Nov. 1, 1997.
Frederick R. Blattner et al., Science, vol. 277:1453–1462, Dec. 5, 1997, The Complete Genome Sequence of *Escherichia coli* K–12.
Hiroji Aiba et al., DNA Research, vol. 3:363–377, 1996, A 570–kb DNA Sequence of the *Escherichia coli* K–12 Genome Corresponding to the 28.0–40.1 min Region on the Linkage Map.
EMBL Sequence Library Accession No: Z18143, Nov. 6, 1992, Desprez, T. et al., The *Arabidopsis Thaliana* Transcribed Genome: the GDR cDNA Program.
EMBL Sequence Library Accession No: N96369, Apr. 19, 1996, Newman, T. et al., Genes Galore: A Summary of Methods for Accessing Results from Large–scale Partial Sequencing of Anonymous Arabidopsis cDNa Clones.
EMBL Sequence Library Accession No: Z18128, Nov. 6, 1992, Desprez, T. et al., The *Arabidopsis Thaliana* Transcribed Genome: the GDR cDNA Program.
Kathleen M. George et al., Journ. of Biol. Chem., vol. 270(45):27292–27298, 1995, The Biosynthesis of Cyclopropanated Mycolic Acids in *Mycobacterium tuberculosis*.
Katherine M. Schmid, Plant Lipid Metabolism, 108–110, Jan. 1, 1995, Dihydrosterculate in Tobacco Transformed with Bacterial Cyclopropane Fatty Acid Synthase.
John B. Ohlrogge et al., Plant Phys., vol. 104:821–826, 1994, Design of New Plant Products: Engineering of Fatty Acid Metabolism.

* cited by examiner

*Primary Examiner*—Phuong T. Bui

(57) ABSTRACT

This invention relates to an isolated nucleic acid fragment encoding a cyclopropane synthetase. The invention also relates to the construction of a chimeric gene encoding all or a portion of the cyclopropane synthetase, in sense or antisense orientation, wherein expression of the chimeric gene results in production of altered levels of the cyclopropane synthetase in a transformed host cell.

13 Claims, 4 Drawing Sheets

FIGURE 1A

```
              *              + +    +  *++++++  *++++++  +++   *   ++++
SEQ ID NO:11  MSSSCIEEVSVPDDNWYRIANELLSRAGIAINGSAPADIRVKNPDFFKRVLQEGSLGLGESYMDGWWECD
SEQ ID NO:02  MVAASVAERAYEAAT---RSALVALERNLI------PDAVTRR----LTRLL------LAQRLRQGYLPSA
SEQ ID NO:04  M--EGMMQLAYDATV--KLMLSALERNLL------PDAVTRR----LTRIL------LATRLRSSSNTSS
              1                                                                    70

*++      + *++++ +    + *+++ + +       +      * ++      +++++*+  +++*
SEQ ID NO:11  RLDMFFSKVLRAGLENQLPHHFKDTLRIAGARLFNLQSKKRAWIVGKEHYDLGNDLFSRMLDPFMQYSCA
SEQ ID NO:02  PLQL---------QQL-LQFVHSLE---EMPIAIETDKAK----AQHYELPTFFKLVLGKNLKYSSC
SEQ ID NO:04  DLQL---------SHL-QHFAHSLQ---EMPIAINTEKPK----SQHYELPTAFFKLVLGSNLKYSCC
                                                                                    140

*+ + +*++*+ *  +  +++++   *   +  +  *   + *++*++ +*++++*+++ ++  +++
SEQ ID NO:11  YWKDADN-LESAQQAKLKMICEKLQLKPGMR VLDIGCWG GLAHYMASNY-DVSVVGVTISAEQQKMAQE
SEQ ID NO:02  YFPGDSSTLEDAEVAMMDLYCERSKLQDGQS ILDVGCWG SLSLYIAKKYRNCSVTGICNSTTQKAFIEE
SEQ ID NO:04  YFSSASMTLEDAEEAMLKYCERSNLTDGHT VLDVGCWG SLALNIPKNYTNCRVTGICNSTTQKAYIEE
              141                                                                  210

*++  +  +  *++++++  +++  + *++  +*+++  +++++  +++  ++++ +*  ++++*++
SEQ ID NO:11  RCEGLD---VTILLQDYR-DLNDQFDRIVSVGMFEHVGPKNYDTYFAVVDRNLKPEGIFLLHTIGSKK-
SEQ ID NO:02  QCRDNELSNIEIIVADISKFEMERSFDRIVSIEMFEHM--KNYKSLLKKISRWMKEDGLLFVHLFCHKAF
SEQ ID NO:04  KCRDLQLQNMNIIVADISTLMEASYDRIFSIEMFEHM--KNYKELLKKISKWMKEDSLLFVHYFCHKAF
              211                                                                  280
```

FIGURE 1B

```
                  +++++*+*  *******+++*   +*+++*******+++++  ++  *  +*++ *  +*   *++++*+++  + +
SEQ ID NO:11      ---TDLNVDPWINKYIFPNGCLPSVRQIAQSSEPHFVMEDWHNFGADYDTTLMAWYER----FLAAWPE
SEQ ID NO:02      PYHFEDKNDDDWITRYFFTGGTMPSANLLLYFQEDVSVVDHWLVSGTHYARTSEEWLKRMDKSITSIRLI
SEQ ID NO:04      AYHFEDKNEDDWITRYFFSGGTMPSANLLLYFQDDVTVINHWLVNGKHYSQTSEEWLKRMDQRMTYIKPI
                  281                                                                350

+*+  +  ++++++*+++++++*+*++ +*++++   + *+ +    + *+  ++
SEQ ID NO:11      IADNYS-ERFKRMFTY---YLNACAGAFRARDIQLMQVVFSRGVENGLRVAR
SEQ ID NO:02      FEETYGKESTTKWIAYWRTFFISVAELFGYNNGDEWMVA------HYLFRKK
SEQ ID NO:04      MQSTYGNDSATKWTAYWRTFFISVAELFGYNNGEEWMVA------HFLFKKK
                  351                                              402
```

FIGURE 2A

```
                    *                  **       ******    *  ******     **    ***       *
SEQ ID NO:02        MVAASVAERAYEAATRSALVALERNLIPDAVTRRLLTRLLLAQRLRQGYLPS----APLQL
SEQ ID NO:04        ME--GMMQLAYDATVKLMLSALERNLLPDAVTRRLTRLLTRILLATRLR----SSSNTSSDLQL
SEQ ID NO:06        MAMAARA--AYLAATRAALAALAALERNALPDAVTRRLTRLLLAQRLRLGYLPSSSSAPLHL
SEQ ID NO:08        ME--GTMQLAYETVVKLMLAALERNVLPDVITRRLTRLLTRLLATRLR---SAYKPSSQLQL
SEQ ID NO:10        MAAAVAARAYEAAARSALAALERNLLPDAVTRRLTRFLLAQRLRLGTLPS----APLQL
                    1                                                            60

*      ******  *   *     *  * ******  *********  **  *    **
SEQ ID NO:02        QQLLQFVHSLEEMPIAIETDKAKAQHYELPTTFFKLVLGKNLKYSSCYFPGDSSTLEDAE
SEQ ID NO:04        SHLQHFAHSLQEMPIAINTEKPKSQHYELPTAFFKLVLGSNLKYSSCCYFSSASMTLEDAE
SEQ ID NO:06        HHLLLFAHALEEMPIAIETEKAKXQHYELPTTFFKLVLGRNLKYSSCYFPDESSTLEDAX
SEQ ID NO:08        SDLLYFAHSLQEMPIAINTDKPKSQHYELPTAFFKLVLGNNLKYSCCYFSSASMTLDDAE
SEQ ID NO:10        QDLLLFAHSLEGMPIAIETDTAKTQHYELPTTFFKLVLGKNLKYSSCYFPDDSSTLEDAE
                    61                                                          120

**   *     *  **          **********  **      *   *******  *
SEQ ID NO:02        VAMMDLYCERSKLQDGQS   ILDVGCGWG   SLSLYIAKKYRNCSVTGICNSTTQKAFIEEQCR
SEQ ID NO:04        EAMLKLYCERSNLTDGHT   VLDVGCGWG   SLALNIPKNYTNCRVTGICNSTTQKAYIEEKCR
SEQ ID NO:06        V
SEQ ID NO:08        EAMLKLYCERSNLKDGHT   VLDVGCGWG   SLALYIAKNYTNCRVTGICNSTTQKAYIEEKCR
SEQ ID NO:10        VAMLELYCERAQLQDGQS   ILDVGCGWG   SLSVYIAKKYRNCNITGICNSTTQKGFIEKQCR
                    121                                                         180
```

FIGURE 2B

```
                       *  * *********  ****************  ****** ****
SEQ ID NO:02           DNELSNIEIIVADISKFEMERSFDRIVSIEMFEHMKNYKSLLKKISRWMKEDGLLFVHLF
SEQ ID NO:04           DLQLQNMNIIVADISTLEMEASYDRIFSIEMFEHMKNYKELLKKISKWMKEDSLLFVHYF
SEQ ID NO:06
SEQ ID NO:08           DLQLQNLNIIVADISTFEMETSYDRIFSIEMFEHMKNYKDLLKKISKWMKEDSLLFVHYF
SEQ ID NO:10           ENELSNVEIIVADISKFEM
                       181                                                         240

******  **********  **  ************************  *  * ****
SEQ ID NO:02           CHKAFPYHFEDKNDDDWITRYFFTGGTMPSANLLLYFQEDVSVVDHWLVSGTHYARTSEE
SEQ ID NO:04           CHKAFAYHFEDKNEDDWITRYFFSGGTMPSANLLLYFQDDVTVINHWLVNGKHYSQTSEE
SEQ ID NO:06
SEQ ID NO:08           CHKAFAYHFEDKNEDDWITRYFFTGGTMPSANLLLY
SEQ ID NO:10
                       241                                                         300

******    *  *    ***  ***  ******************* ******  ** **
SEQ ID NO:02           WLKRMDKSITSIRLIFEETYGKESTTKWIAYWRTFFISVAELFGYNNGDEWMVAHYLFRKK
SEQ ID NO:04           WLKRMDQRMTYIKPIMQSTYGNDSATKWTAYWRTFFISVAELFGYNNGEEWMVAHFLFKKK
SEQ ID NO:06
SEQ ID NO:08
SEQ ID NO:10
                       301                                                         360
```

CYCLOPROPANE-FATTY-ACYL-PHOSPHOLIPID SYNTHASE

This application is a continuation of International Application No. PCT/US99/03455, filed Feb. 18, 1999, which claims the benefit of U.S. Provisional Application No. 60/076,203, filed Feb. 27, 1998.

FIELD OF THE INVENTION

This invention is in the field of plant molecular biology. More specifically, this invention pertains to nucleic acid fragments encoding cyclopropane synthetase in plants and seeds.

BACKGROUND OF THE INVENTION

Plant oils and lipids are central to the plant membrane function and climatic adaptation and have a variety of nutritional and industrial uses. Production of oils with a modified fatty acid spectrum and improved functional characteristics is a major goal of the agricultural and food industry. Lipids represent a vast array of chemical structures many of which result, directly or indirectly, from metabolic processes that alter the degree of saturation (or unsaturation) and/or add functional groups to the lipids. These groups may be hydroxyls, ketones, epoxys, cyclopentenyl, cyclopropyl, furans or halogens. Using genetic engineering to change the activity of enzymes involved in the biosynthesis of lipids represents an attractive target for altering the levels of specific lipid structures in plants. Changes in the lipid profile will result in plants with superior oil qualities such as functional stability and/or taste. These plants will have considerable importance and value.

Cyclopropane-fatty-acyl-phospholipid synthase (EC 2.1.1.79) is also called cyclopropane synthetase or unsaturated-phospholipid methyltransferase. This enzyme adds a methylene group across the 9,10 position of a delta9-olefinic acyl chain in phosphatidylethanolamine or, more slowly, phosphatidylglycerol or phosphatidylinositol forming a cyclopropane deirvative. It transfers a methylene group from S-adenosyl-1-methionine to the cis double bond of the unsaturated fatty acid chain resulting in the replacement of the double bond with a methylene bridge. Cyclopropane synthetase from bacteria such as *Escherichia coli* and *Mycobacterium tubeculosis* has been isolated and their gene identified (Taylor, F. R. et al. (1981) *Methods Enzymol* 71:133–139; Grogan, D. W. and Cronan, J. E. Jr. (1984) *J Bacteriol* 158:286–295; Yuan, Y. et al. (1985) *Proc Natl Acad Sci USA* 92:6630–6634). No cycloprane synthetase has been identified to date in plants. Identification of the genes involved in the modification and saturation of lipids in plants is important for the development of industrially-important oil crops.

SUMMARY OF THE INVENTION

The instant invention relates to isolated nucleic acid fragments encoding cyclopropane synthetase. Specifically, this invention concerns an isolated nucleic acid fragment encoding a cyclopropane synthetase. In addition, this invention relates to a nucleic acid fragment that is complementary to the nucleic acid fragment encoding cyclopropane synthetase.

An additional embodiment of the instant invention pertains to a polypeptide encoding all or a substantial portion of a cyclopropane synthetase.

In another embodiment, the instant invention relates to a chimeric gene encoding cyclopropane synthetase, or to a chimeric gene that comprises a nucleic acid fragment that is complementary to a nucleic acid fragment encoding a cyclopropane synthetase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a cyclopropane synthetase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a cyclopropane synthetase in a transformed host cell comprising: a) transforming a host cell with a chimeric gene comprising a nucleic acid fragment encoding a cyclopropane synthetase; and b) growing the transformed host cell under conditions that are suitable for expression of the chimeric gene wherein expression of the chimeric gene results in production of altered levels of cyclopropane synthetase in the transformed host cell.

An addition embodiment of the instant invention concerns a method for obtaining a nucleic acid fragment encoding all or a substantial portion of an amino acid sequence encoding a cyclopropane synthetase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A and 1B depict the amino acid sequence alignment between the cyclopropane synthetase from a corn contig assembled from clones cs1.pk0064.b1, cs1.pk0063.c3 and p0095.cwsbu56r (SEQ ID NO:2) amino acids 29–385, Phaseolus clone plht.pk0008.c7 (SEQ ID NO:4) and *Escherichia coli* (NCBI gi Accession No. 231731, SEQ ID NO:11). Amino acids which are conserved among all sequences are indicated with an asterisk (*) while those conserved only within the plant sequences are indicated by a plus sign (+). Amino acids belonging to the putative S-adenosyl-L-methionine binding motif are boxed in black and displayed in white. Dashes are used by the program to maximize alignment of the sequences. FIG. 1A, amino acids 1 through 280. FIG. 1B, amino acids 281 through 402.

FIGS. 2A and 2B depict the amino acid sequence alignment between the cyclopropane synthetase from corn contig assembled from clones cs1.pk0064.b1, cs1.pk0063.c3 and p0095.cwsbu56r (SEQ ID NO:2)amino acids 29–385, Phaseolus clone plht.pk0008.c7 (SEQ ID NO:4), rice clone r10n.pk082.o15 (SEQ ID NO:6), soybean clone sfl1.pk0071.c10 (SEQ ID NO:8) amino acids 29 through 384 and wheat contig assembled from clones wl1n.pk0095.e7 and wlmk1.pk0027.d11 (SEQ ID NO:10). Amino acids which are conserved among all sequences are indicated with an asterisk (*). Amino acids belonging to the putative S-adenosyl-L-methionine binding motif are boxed in black and displayed in white. Dashes are used by the program to maximize alignment of the sequences. FIG. 2A, amino acids 1 through 280. FIG. 2B, amino acids 181 through 360.

The following sequence descriptions and Sequence Listing attached hereto comply with the rules governing nucleotide and/or amino acid sequence disclosures in patent applications as set forth in 37 C.F.R. §1.821–1.825.

SEQ ID NO: 1 is the nucleotide sequence comprising the contig assembled from the entire cDNA insert in clone cs1.pk0064.b1 and a portion of the cDNA insert in clones cs1.pk0063.c3 and p0095.cwsbu56r encoding an entire corn cyclopropane synthetase with a portion of its signal sequence.

SEQ ID NO:2 is the deduced amino acid sequence of an entire corn cyclopropane synthetase with a portion of its signal sequence derived from the nucleotide sequence of SEQ ID NO: 1. The mature synthase without its signal sequence consists of amino acids 29 through 385.

SEQ ID NO:3 is the nucleotide sequence comprising the entire cDNA insert in clone plht.pk0008.c7 encoding an entire *Phaseolus lunatus* cyclopropane synthetase.

SEQ ID NO:4 is the deduced amino acid sequence of an entire *Phaseolus lunatus* cyclopropane synthetase derived from the nucleotide sequence of SEQ ID NO:3.

SEQ ID NO:5 is the nucleotide sequence comprising a portion of the cDNA insert in clone rl0n.pk082.o15 encoding the N-terminal third of a rice cyclopropane synthetase.

SEQ ID NO:6 is the deduced amino acid sequence of the N-terminal third of a rice cyclopropane synthetase derived from the nucleotide sequence of SEQ ID NO:5.

SEQ ID NO:7 is the nucleotide sequence comprising a portion of the cDNA insert in clone sfl1.pk0071.c10 encoding a substantial portion of a soybean cyclopropane synthetase with a portion of its signal sequence.

SEQ ID NO:8 is the deduced amino acid sequence of a substantial portion of a soybean cyclopropane synthetase with a portion of its signal sequence derived from the nucleotide sequence of SEQ ID NO:7. The mature synthase without its signal sequence consists of amino acids 29 through 384.

SEQ ID NO:9 is the nucleotide sequence comprising a contig assembled form a portion of the cDNA insert in clones wl1n.pk0095.e7 and wlmk1.pk0027.d11 encoding a substantial portion of a wheat cyclopropane synthetase.

SEQ ID NO: 10 is the deduced amino acid sequence of a portion of a wheat cyclopropane synthetase derived from the nucleotide sequence of SEQ ID NO:9.

SEQ ID NO: 11 is the amino acid sequence of an *Escherichia coli* cyclopropane synthetase NCBI General Identifier No. 23173.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence similarity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under stringent conditions (0.1×SSC, 0.1% SDS, 65° C.), with the sequences exemplified herein.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the cyclopropane synthetase proteins as set forth in SEQ ID NOs:2, 4, 6, 8 and 10. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several cyclopropane synthetases have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Cyclopropane Synthetase

| Enzyme | Clone | Plant |
| --- | --- | --- |
| Cyclopropane synthetase | Contig of:<br>cs1.pk0064.b1:fis<br>cs1.pk0063.c3<br>p0095.cwsbu56r | Corn |
| | plht.pk0008.c7 | Phaseolus |
| | rl0n.pk082.o15 | Rice |
| | sfl1.pk0071.c10 | Soybean |
| | Contig of:<br>wl1n.pk0095.e7<br>wlmk1.pk0027.d11 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other cyclopropane synthetases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed cyclopropane synthetases are present at higher or lower levels than normal or in cell types or developmental stages in which they are not normally found. This would have the effect of altering the level of cyclopropane fatty acids in those cells. Manipulation of the activity of cyclopropane synthetase in plants will allow the production of lipids with different degrees of saturation in those cells.

Overexpression of the cyclopropane synthetase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant cyclopropane synthetase to different cellular compartments, or to facilitate its secretion from the cell. It is thus envisioned that the chimeric gene described above may be further supplemented by altering the coding sequence to encode cyclopropane synthetase with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding cyclopropane synthetase in plants for some applications. In order to accomplish this, a chimeric gene designed for co-suppression of the instant cyclopropane synthetase can be constructed by linking a gene or gene fragment encoding a cyclopropane synthetase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant cyclopropane synthetases (or portions thereof) may be produced in heterologous host cells, particularly in the cells of microbial hosts, and can be used to prepare antibodies to the these proteins by methods well known to those skilled in the art. The antibodies are useful for detecting cyclopropane synthetase in situ in cells or in vitro in cell extracts. Preferred heterologous host cells for production of the instant cyclopropane synthetase are microbial hosts. Microbial expression systems and expression vectors containing regulatory sequences that direct high level expression of foreign proteins are well known to those skilled in the art. Any of these could be used to construct a chimeric gene for production of the instant cyclopropane synthetase. This chimeric gene could then be introduced into appropriate microorganisms via transformation to provide high level expression of the encoded cyclopropane synthetase. An example of a vector for high level expression of the instant cyclopropane synthetase in a bacterial host is provided (Example 6).

Additionally, the instant cyclopropane synthetase can be used as a target to facilitate design and/or identification of inhibitors of those enzymes that may be useful as herbicides. This is desirable because the cyclopropane synthetases described herein catalyzes the transfer of methionine from S-adenosyl-1-methionine to a phospholipid olefinic fatty acid. Accordingly, inhibition of the activity of the enzyme described herein could lead to inhibition plant growth. Thus, the instant cyclopropane synthetase could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the cyclopropane synthetase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a cyclopropane synthetase can be identified and obtained. This mutant plant can then be used to determine or confirm the natural function of the cyclopropane synthetase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, Phaseolus, rice, soybean and wheat tissues were prepared. The characteristics of the libraries are described below.

TABLE 2 cDNA Libraries from Corn, Phaseolus, Rice, Soybean and Wheat

| Library | Tissue | Clone |
|---|---|---|
| cs1 | Corn Leaf Sheath From 5 Week Old Plant | cs1.pk0063.c3 cs1.pk0064.b1:fis |
| p0095 | Corn Ear Leaf Sheath, 2 to 3 Weeks After Pollen Shed | p0095.cwsbu56r |
| plht | Heat Tolerant *Phaseolus lunatus* Leaf | plht.pk0008.c7 |
| rl0n | Rice 15 Day Old Leaf* | rl0n.pk082.o15 |
| sfl1 | Soybean Immature Flower | sfl1.pk0071.c10 |
| wl1n | Wheat Leaf From 7 Day Old Seedling* | wl1n.pk0095.e7 |
| wlmk1 | Wheat Seedlings 1 Hour After Inoculation With *Erysiphe graminis f.* sp *tritici* and Treatment With Herbicide** | wlmk1.pk0027.d11 |

*These libraries were normalized essentially as described in U.S. Pat. No. 5,482,845
**Application of 6-iodo-2-propoxy-3-propyl-4(3H)-quinazolinone; synthesis and methods of using this compound are described in USSN 08/545,827, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding cyclopropane synthetase were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Cyclopropane Synthetase

The BLASTX search using the EST sequences from clones plht.pk0022.d12 and plht.pk0011.f3 revealed similarity of proteins encoded by the cDNAs to cyclopropane synthetase from *Mycobacterium tuberculosis* (GenBank Accession No. Z77162). The BLASTX search using the EST sequences from clone cs1.pk0064.b1 and rlr48.pk0006.h3 revealed similarity of proteins encoded by the cDNAs to cyclopropane synthetase from *E. coli* (GenBank Accession No. M98330). The BLASTX search using the EST sequences from clone wl1n.pk0095.e7 revealed similarity of protein encoded by the cDNA to cyclopropane synthetase from *Mycobacterium tuberculosis* (SWISS-PROT Accession No. Q11195). The BLASTX results for each of these ESTs are shown in Table 3:

TABLE 3

BLASTX Results for Clones Encoding Polypeptides Homologous to Cyclopropane Synthetase

| Clone | Database | Accession No. | Organism | pLog |
|---|---|---|---|---|
| cs1.pk0064.b1 | GenBank | M98330 | *E. coli* | 20.10 |
| plht.pk0022.d12 | GenBank | Z77162 | *Mycobacterium tuberculosis* | 15.54 |
| plht.pk0011.f3 | GenBank | Z77162 | *Mycobacterium tuberculosis* | 6.70 |

TABLE 3-continued

BLASTX Results for Clones Encoding Polypeptides Homologous to Cyclopropane Synthetase

| Clone | Database | Accession No. | Organism | pLog |
| --- | --- | --- | --- | --- |
| rlr48.pk0006.h3 | GenBank | M98330 | E. coli | 10.38 |
| wl1n.pk0095.e7 | SWISS-PROT | Q11195 | Mycobacterium tuberculosis | 13.00 |

EST sequences from clones plht.pk0022.d12 and rlr48.pk0006.h3 were used to search a plant cDNA database using TBLASTX to find other cDNAs that encode plant cyclopropane synthetases. (The TBLASTX algorithm uses the basic BLAST algorithm to translate the nucleotide sequence of the query EST in all six reading frames and compare the translation to cDNAs of the database likewise translated in all six reading frames. The TBLASTX search using the EST sequences from clones plht.pk0022.d12 and rlr48.pk0006.h3 revealed similarity of proteins encoded by the cDNAs to cyclopropane synthetase from various plants. The TBLASTX results from a search with clone plht.pk0022.d12 are presented in Table 4; the TBLASTX results from a search with clone rlr48.pk0006.h3 are presented in Table 5:

TABLE 4

TBLASTX Results for Clones Encoding Polypeptides Homologous to Cyclopropane Synthetase Encoded by plht.pk0022.d12

| Clone | pLog |
| --- | --- |
| plht.pk0011.f3 | 68.70 |
| plht.pk0008.c7 | 44.50 |
| se5.pk0023.e12 | 18.00 |
| sfl1.pk0071.c10 | 54.30 |
| sfl1.pk0034.g5 | 43.50 |
| sfl1.pk0034.g6 | 25.00 |
| wl1n.pk0095.e7 | 42.00 |

TABLE 5

TBLASTX Results for Clones Encoding Polypeptides Homologous to Cyclopropane Synthetases Encoded by rlr48.pk0006.h3

| Clone | pLog |
| --- | --- |
| rls6.pk0061.e5 | 37.00 |

TBLASTN analysis of the proprietary plant EST database indicated that other corn clones besides cs1.pk0064.b1 encoded cyclopropane synthetase. A contig was assembled using the sequence from a portion of the cDNA inserts in clones cs1.pk0063.c3 and p0095.cwsbu56r and the entire cDNA insert from clone cs1.pk0064.b1. The sequence of this contig is shown in SEQ ID NO: 1; the deduced amino acid sequence of this cDNA is shown in SEQ ID NO:2. This amino acid sequence contains a signal sequence (amino acids 1–28) and a mature protein (amino acids 29–385). The sequence of the entire cDNA insert from clone plht.pk0008.c7 was determined and is shown in SEQ ID NO:3; the deduced amino acid sequence of this cDNA is shown in SEQ ID NO:4. The sequence in SEQ ID NO:3 includes the sequences from clones plht.pk0011.f3 and plht.pk0022.d12. The sequence of most of the cDNA insert from clone sfl1.pk0071.c10 has been determined and is shown in SEQ ID NO:7; the deduced amino acid sequence of this cDNA is shown in SEQ ID NO:8. This amino acid sequence contains a signal sequence (amino acids 1–28) and a portion of a mature protein (amino acids 29–299). The nucleotide sequence in SEQ ID NO:7 includes the sequences from clones sfl1.pk0034.g5 and sfl1.pk0034.g6. The clone se5.pk0023.e12 is not included since it encodes a portion of a soybean cyclopropane synthetase which falls inside SEQ ID NO:8. TBLASTN analysis of the proprietary plant EST database indicated that other wheat clones besides wl1n.pk095.e7 encoded cyclopropane synthetase. A contig was assembled using the sequence from a portion of the cDNA inserts in clones wl1n.pk0095.e7 and wlmk1.pk0027.d11. The sequence of this contig is shown in SEQ ID NO:9; the deduced amino acid sequence of this cDNA is shown in SEQ ID NO: 10.

The BLASTX search using the nucleotide sequences mentioned above revealed similarity of the proteins encoded by the cDNAs to cyclopropane synthetase from *Escherichia coli* or *Mycobacterium tuberculosis* (NCBI General Identifier Nos. 231731 and 1705757, respectively). The BLASTX results for each of these sequences are shown in Table 6:

TABLE 6

BLAST Results for Clones Encoding Polypeptides Homologous to Cyclopropane Synthetase

| Clone | NCBI General Identifier No. | BLAST pLog Score |
| --- | --- | --- |
| Contig of cs1.pk0064.b1:fis cs1.pk0063.c3 p0095.cwsbu56r | 231731 | 23.5 |
| plht.pk0008.c7 | 231731 | 20.7 |
| sfl1.pk0071.c10 | 231731 | 20.0 |
| Contig of wl1n.pk0095.e7 wlmk1.pk0027.d11 | 1705757 | 13.1 |

FIG. 1 presents an alignment of the amino acid sequences set forth in SEQ ID NO:2 and SEQ ID NO:4 with the *Escherichia coli* sequence (SEQ ID NO:11). The *Escherichia coli* sequence is 19.95% similar to the amino acid sequence presented in SEQ ID NO:2 and it is 19.2% similar to the amino acid sequence presented in SEQ ID NO:4.

TBLASTN analysis of the proprietary plant EST database using the sequences from clone sfl1.pk0071.c10 revealed a rice clone (rl0n.pk082.o15) with similarities to the soybean cyclopropane synthetase with a pLog value of 16.7. The sequence of a portion of the cDNA insert in clone rl0n.pk082.o15 is shown in SEQ ID NO:5; the deduced amino acid sequence of this cDNA is shown in SEQ ID NO:6. FIG. 2 presents an alignment of the amino acid sequences set forth in SEQ ID NO:2, SEQ ID NO:4, SEQ ID NO:6, SEQ ID NO:8 and SEQ ID NO:10. The amino acid sequence set forth in SEQ ID NO:2 is 72.4% similar to the amino acid sequence set forth in SEQ ID NO:4.

Sequence alignments and percent similarity calculations were performed using the Megalign program of the LASAR- GENE bioinformatics computing suite (DNASTAR Inc., Madison, Wis.). Multiple alignment of the sequences and percent similarity calculations were performed using the Clustal method of alignment (Higgins, D. G. and Sharp, P. M. (1989) *CABIOS*. 5:151–153) using the default parameters (GAP PENALTY=10, GAP LENGTH PENALTY=10).

Sequence alignments and BLAST scores and probabilities indicate that the instant nucleic acid fragments encode entire corn and phaseolus and substantial portions of rice, soybean and wheat cyclopropane synthetase. These sequences represent the first plant sequences encoding cyclopropane synthetase.

Example 4

Expression of Chimeric Genes in Monocot Cells

A chimeric gene comprising a cDNA encoding cyclopropane synthetase in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding cyclopropane synthetase, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfturt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 $\mu$m in diameter) are coated with DNA using the following technique. Ten $\mu$g of plasmid DNAs are added to 50 $\mu$L of a suspension of gold particles (60 mg per mL). Calcium chloride (50 $\mu$L of a 2.5 M solution) and spermidine free base (20 $\mu$L of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 $\mu$L of absolute ethanol, centrifuged again and the supernatant removed. The ethanol rinse is performed again and the particles resuspended in a final volume of 30 $\mu$L of ethanol. An aliquot (5 $\mu$L) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 5

Expression of Chimeric Genes in Dicot Cells

A seed-specific expression cassette composed of the promoter and transcription terminator from the gene encoding the $\beta$ subunit of the seed storage protein phaseolin from the bean *Phaseolus vulgaris* (Doyle et al. (1986) *J. Biol. Chem.*

261:9228–9238) can be used for expression of the instant cyclopropane synthetase in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding cyclopropane synthetase. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the cyclopropane synthetase and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/ particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant cyclopropane synthetase can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the cyclopropane synthetase are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Crude, partially purified or purified enzyme, either alone or as a fusion protein, may be utilized in assays for the evaluation of compounds for their ability to inhibit enzymatic activation of the cyclopropane synthetases disclosed herein. Assays may be conducted under well known experimental conditions which permit optimal enzymatic activity. Assays for cyclopropane synthetase are presented by Wang, A. Y. et al. (1992) *Biochemistry* 31:11020–11018.

What is claimed is:

1. An isolated polynucleotide comprising:
   (a) a nucleotide sequence encoding a polypeptide having cyclopropane synthetase activity, wherein the amino acid sequence of the polypeptide and the amino acid sequence of amino acids 29–385 of SEQ ID NO:2 have at least 80% sequence identity based on the Clustal alignment method, or
   (b) the complement of the nucleotide sequence, wherein the complement and the nucleotide sequence contain the same number of nucleotides and are 100% complementary.

2. The polynucleotide of claim 1 wherein the amino acid sequence of the polypeptide and the amino acid sequence of amino acids 29–385 of SEQ ID NO:2 have at least 90% sequence identity based on the Clustal alignment method.

3. The polynucleotide of claim 1 wherein the amino acid sequence of the polypeptide and the amino acid sequence of amino acids 29–385 of SEQ ID NO:2 have at least 95% sequence identity based on the Clustal alignment method.

4. The polynucleotide of claim 1 wherein the polypeptide comprises the amino acid sequence of amino acids 29–385 of SEQ ID NO:2.

5. The polynucleotide of claim 1 wherein the polypeptide comprises the amino acid sequence of SEQ ID NO:2.

6. The polynucleotide of claim 1 wherein the nucleotide sequence comprises the nucleotide sequence of SEQ ID NO: 1.

7. A vector comprising the polynucleotide of claim 1.

8. A recombinant DNA construct comprising the polynucleotide of claim 1 operably linked to a regulatory sequence.

9. A method for transforming a cell comprising transforming a cell with the polynucleotide of claim 1.

10. A cell comprising the recombinant DNA construct of claim 8.

11. A method for producing a plant comprising transforming a plant cell with the polynucleotide of claim 1 and regenerating a plant from the transformed plant cell.

12. A plant comprising the recombinant DNA construct of claim 8.

13. A seed comprising the recombinant DNA construct of claim 8.

* * * * *

SEQUENCE LISTING

<160> NUMBER OF SEQ ID NOS: 11

<210> SEQ ID NO 1
<211> LENGTH: 1314
<212> TYPE: DNA
<213> ORGANISM: Zea mays

<400> SEQUENCE: 1

```
gatctaatag cgccgcaacg cgaagcgcga agccgcgaag cctcgcctgt ctggtcagtt      60
ccttcgcgca ccggcaccgc ggcggcagtt cagcatggtg gcagcatccg tagccgagcg     120
ggcctatgag gcggcgacgc ggtccgcgct ggtggcgctg gagcgcaacc tcatcccgga     180
cgcggtgacc cggcgcctga cgcggctcct gctagcgcag cgcctccgcc agggctacct     240
cccctccgcg ccgctccagc tgcagcagct cctccagttc gtccactctc ttgaagagat     300
gcccattgcc attgaaacag acaaagctaa agcccaacac tatgagttgc caactacatt     360
tttcaagcta gtgctgggaa agaatctcaa atacagttcc tgctatttcc ctggtgattc     420
aagcacccta gaagatgctg aggttgcgat gatggatctg tattgtgaga ggtcgaaact     480
acaagatggc caaagtatcc tagatgttgg atgtggatgg ggatcccttt cactgtacat     540
tgcaaagaaa tataggaact gcagtgtaac agggatatgc aactctacta cacagaaggc     600
ttttatagaa gagcaatgta gggataacga gctgtcaaat attgagataa tcgtagccga     660
catcagcaag tttgagatgg agcgctcttt tgacaggatc gtatctatag agatgtttga     720
gcacatgaaa aactacaagt cgcttcttaa gaagatatcc aggtggatga agaggatgg     780
cctactattc gttcacctct tctgccacaa agcatttcca tatcactttg aggataaaaa     840
cgatgatgac tggatcacga ggtatttctt cactggagga acaatgccat ctgcaaacct     900
acttctatac tttcaggagg atgtatctgt ggtagatcat tggcttgtca gtggcacgca     960
ttatgctaga actagcgagg agtggctaaa acgtatggac aagagcatca cttcaataag    1020
gctgatcttc gaggaaactt atgggaagga atcgactacc aaatggatag cttattggcg    1080
gacgttcttc atctcggtag ctgaactttt tggatacaac aatggagatg aatggatggt    1140
tgcccattac ttgttccgaa agaagtagag gctactgctt ggaagtaccc aatcaaaaat    1200
caatgttttc agtaattttg tcatgtacat cgacgaacaa ctccttttct ggcacgtagt    1260
tgtatctcgt accgacttcg tagtggtttc aaaaacaaaa aaaaaaaaaa aaaa          1314
```

<210> SEQ ID NO 2
<211> LENGTH: 385
<212> TYPE: PRT
<213> ORGANISM: Zea mays

```
<400> SEQUENCE: 2

Arg Arg Asn Ala Lys Arg Glu Ala Ala Lys Pro Arg Leu Ser Gly Gln
 1               5                  10                  15

Phe Leu Arg Ala Pro Ala Pro Arg Gln Phe Ser Met Val Ala Ala
            20                  25                  30

Ser Val Ala Glu Arg Ala Tyr Glu Ala Ala Thr Arg Ser Ala Leu Val
            35                  40                  45

Ala Leu Glu Arg Asn Leu Ile Pro Asp Ala Val Thr Arg Arg Leu Thr
50                  55                  60

Arg Leu Leu Leu Ala Gln Arg Leu Arg Gln Gly Tyr Leu Pro Ser Ala
65                  70                  75                  80

Pro Leu Gln Leu Gln Gln Leu Leu Gln Phe Val His Ser Leu Glu Glu
                85                  90                  95

Met Pro Ile Ala Ile Glu Thr Asp Lys Ala Lys Ala Gln His Tyr Glu
            100                 105                 110

Leu Pro Thr Thr Phe Phe Lys Leu Val Leu Gly Lys Asn Leu Lys Tyr
            115                 120                 125

Ser Ser Cys Tyr Phe Pro Gly Asp Ser Ser Thr Leu Glu Asp Ala Glu
130                 135                 140

Val Ala Met Met Asp Leu Tyr Cys Glu Arg Ser Lys Leu Gln Asp Gly
145                 150                 155                 160

Gln Ser Ile Leu Asp Val Gly Cys Gly Trp Gly Ser Leu Ser Leu Tyr
                165                 170                 175

Ile Ala Lys Lys Tyr Arg Asn Cys Ser Val Thr Gly Ile Cys Asn Ser
            180                 185                 190

Thr Thr Gln Lys Ala Phe Ile Glu Glu Gln Cys Arg Asp Asn Glu Leu
            195                 200                 205

Ser Asn Ile Glu Ile Ile Val Ala Asp Ile Ser Lys Phe Glu Met Glu
210                 215                 220

Arg Ser Phe Asp Arg Ile Val Ser Ile Glu Met Phe Glu His Met Lys
225                 230                 235                 240

Asn Tyr Lys Ser Leu Leu Lys Lys Ile Ser Arg Trp Met Lys Glu Asp
                245                 250                 255

Gly Leu Leu Phe Val His Leu Phe Cys His Lys Ala Phe Pro Tyr His
            260                 265                 270

Phe Glu Asp Lys Asn Asp Asp Trp Ile Thr Arg Tyr Phe Phe Thr
            275                 280                 285

Gly Gly Thr Met Pro Ser Ala Asn Leu Leu Leu Tyr Phe Gln Glu Asp
290                 295                 300

Val Ser Val Val Asp His Trp Leu Val Ser Gly Thr His Tyr Ala Arg
305                 310                 315                 320

Thr Ser Glu Glu Trp Leu Lys Arg Met Asp Lys Ser Ile Thr Ser Ile
                325                 330                 335

Arg Leu Ile Phe Glu Glu Thr Tyr Gly Lys Glu Ser Thr Thr Lys Trp
            340                 345                 350

Ile Ala Tyr Trp Arg Thr Phe Phe Ile Ser Val Ala Glu Leu Phe Gly
            355                 360                 365

Tyr Asn Asn Gly Asp Glu Trp Met Val Ala His Tyr Leu Phe Arg Lys
370                 375                 380

Lys
385

<210> SEQ ID NO 3
```

<210> SEQ ID NO 3
<211> LENGTH: 1412
<212> TYPE: DNA
<213> ORGANISM: Phaseolus lunatus

<400> SEQUENCE: 3

```
gcacgaggaa gaagataaga cacagtagga gaattgtaga actgtgggtg ctacttaccg      60
ttcttgcttc tgcactgaag gttcccctgc gcgtgggctt ccatggaagg gatgatgcag     120
cttgcatatg acgctacggt gaagctcatg ctgtctgcac tcgagcgcaa cctgctacct     180
gacgccgtca ccaggagact cacgcgcatc cttttggcta ctcgccttcg ctcttcttcc     240
aacacatcct cggatcttca gctttcacac ctccaacatt tcgcacattc tttacaagag     300
atgcccatag caatcaacac tgagaagccg aaatctcaac attatgaatt accaacagct     360
ttcttcaagc tcgtccttgg aagcaatctc aaatacagct gttgctattt ctcttctgcc     420
tcaatgacgc tggaagatgc tgaagaagca atgttgaaac tgtactgcga gagatcaaac     480
ctcacagatg gtcatacagt acttgatgtg ggatgtggtt ggggatcgct agctttaaac     540
attcccaaga attacactaa ctgcagagtt acaggaatct gcaattctac aactcaaaag     600
gcttatattg aggagaagtg ccgggatctt cagctgcaaa atatgaatat tatagttgct     660
gatattagca cgttggaaat ggaagcttct tatgacagaa tattttccat agaaatgttt     720
gagcatatga agaactacaa agagcttctc aagaagatat ccaaatggat gaaagaggat     780
agccttttat ttgtgcatta cttctgccac aaagcatttg cctaccactt tgaggacaaa     840
aatgaagatg actggattac aagatacttc ttttctggag gaactatgcc gtcagcaaat     900
ctacttcttt attttcaaga tgatgttaca gtcatcaacc attggctagt aaatgggaaa     960
cactactcac aaaccagtga gaatggcttt aaaagaatgg accagagaat gacttacatc    1020
aagccaatta tgcaatcaac ttatggcaat gattcagcaa ccaagtggac tgcctattgg    1080
agaacattct tcatatctgt agcggaactt ttcggataca ataacggtga agaatggatg    1140
gttgcacact tcttttcaa aaagaaataa aataagccaa acctaatct tttaatttga    1200
ctatttaaga atggcttcca aacctatttg actatttgtc ctaagtagtc aggacaaagt    1260
aacctgccaa tcgaagttgc aatttcaata atgttgtgta cttaattaat ttagtttaat    1320
tggttgtcat gaacttttaaa cttaattatg ataaaatcta tttaataaaa tgaagtatgt    1380
atctatttat atataaaaaa aaaaaaaaaa aa                                  1412
```

<210> SEQ ID NO 4
<211> LENGTH: 355
<212> TYPE: PRT
<213> ORGANISM: Phaseolus lunatus

<400> SEQUENCE: 4

```
Met Glu Gly Met Met Gln Leu Ala Tyr Asp Ala Thr Val Lys Leu Met
 1               5                  10                  15

Leu Ser Ala Leu Glu Arg Asn Leu Leu Pro Asp Ala Val Thr Arg Arg
            20                  25                  30

Leu Thr Arg Ile Leu Leu Ala Thr Arg Leu Arg Ser Ser Ser Asn Thr
        35                  40                  45

Ser Ser Asp Leu Gln Leu Ser His Leu Gln His Phe Ala His Ser Leu
    50                  55                  60

Gln Glu Met Pro Ile Ala Ile Asn Thr Glu Lys Pro Lys Ser Gln His
65                  70                  75                  80

Tyr Glu Leu Pro Thr Ala Phe Phe Lys Leu Val Leu Gly Ser Asn Leu
                85                  90                  95
```

```
Lys Tyr Ser Cys Cys Tyr Phe Ser Ser Ala Ser Met Thr Leu Glu Asp
            100                 105                 110

Ala Glu Glu Ala Met Leu Lys Leu Tyr Cys Glu Arg Ser Asn Leu Thr
        115                 120                 125

Asp Gly His Thr Val Leu Asp Val Gly Cys Gly Trp Gly Ser Leu Ala
    130                 135                 140

Leu Asn Ile Pro Lys Asn Tyr Thr Asn Cys Arg Val Thr Gly Ile Cys
145                 150                 155                 160

Asn Ser Thr Thr Gln Lys Ala Tyr Ile Glu Lys Cys Arg Asp Leu
                165                 170                 175

Gln Leu Gln Asn Met Asn Ile Ile Val Ala Asp Ile Ser Thr Leu Glu
        180                 185                 190

Met Glu Ala Ser Tyr Asp Arg Ile Phe Ser Ile Glu Met Phe Glu His
        195                 200                 205

Met Lys Asn Tyr Lys Glu Leu Leu Lys Lys Ile Ser Lys Trp Met Lys
        210                 215                 220

Glu Asp Ser Leu Leu Phe Val His Tyr Phe Cys His Lys Ala Phe Ala
225                 230                 235                 240

Tyr His Phe Glu Asp Lys Asn Glu Asp Asp Trp Ile Thr Arg Tyr Phe
                245                 250                 255

Phe Ser Gly Gly Thr Met Pro Ser Ala Asn Leu Leu Leu Tyr Phe Gln
                260                 265                 270

Asp Asp Val Thr Val Ile Asn His Trp Leu Val Asn Gly Lys His Tyr
            275                 280                 285

Ser Gln Thr Ser Glu Glu Trp Leu Lys Arg Met Asp Gln Arg Met Thr
        290                 295                 300

Tyr Ile Lys Pro Ile Met Gln Ser Thr Tyr Gly Asn Asp Ser Ala Thr
305                 310                 315                 320

Lys Trp Thr Ala Tyr Trp Arg Thr Phe Phe Ile Ser Val Ala Glu Leu
                325                 330                 335

Phe Gly Tyr Asn Asn Gly Glu Glu Trp Met Val Ala His Phe Leu Phe
                340                 345                 350

Lys Lys Lys
        355

<210> SEQ ID NO 5
<211> LENGTH: 481
<212> TYPE: DNA
<213> ORGANISM: Oryza sativa
<220> FEATURE:
<221> NAME/KEY: unsure
<222> LOCATION: (256)
<223> OTHER INFORMATION: n = A, C, G, or T
<220> FEATURE:
<221> NAME/KEY: unsure
<222> LOCATION: (446)
<223> OTHER INFORMATION: n = A, C, G, or T
<220> FEATURE:
<221> NAME/KEY: unsure
<222> LOCATION: (476)
<223> OTHER INFORMATION: n = A, C, G, or T

<400> SEQUENCE: 5
cttacaccac accgggggc taatgctatc cttccttcca agttccaact aaacagaagc     60
gacgcagcaa ggcacagctg ggccgccgac aatggcgatg gcggcgcggg cggcgtacct    120
ggcggcgacg cgcgcggcgc tggcggcgct ggagcgcaac gccctccccg acgcggtcac    180
ccggcgcctg acgcggctgc tgctcgcgca gcgcctccgc ctcggctacc tcccctcctc    240
```

```
ctcctcctcc gcgccnctcc acctccacca cctcctcctc ttcgcccacg ctctagaaga    300
gatgcccatc gcaatcgaga cggagaaagc taaagaccaa gcactacgag ttgcccacga    360 cattttttcaa gctggttctt ggaaggaatc tcaagtacag ctcatgttac ttccctgacg   420
aatcgagcac ccttgaagat gccgangttc aatgctggag ctatattgta aaaggncaat    480
g                                                                    481
```

```
<210> SEQ ID NO 6
<211> LENGTH: 119
<212> TYPE: PRT
<213> ORGANISM: Oryza sativa
<220> FEATURE:
<221> NAME/KEY: UNSURE
<222> LOCATION: (82)
<223> OTHER INFORMATION: Xaa = ANY AMINO ACID
<220> FEATURE:
<221> NAME/KEY: UNSURE
<222> LOCATION: (118)
<223> OTHER INFORMATION: Xaa = ANY AMINO ACID

<400> SEQUENCE: 6
```

```
Met Ala Met Ala Ala Arg Ala Ala Tyr Leu Ala Ala Thr Arg Ala Ala
 1               5                  10                  15

Leu Ala Ala Leu Glu Arg Asn Ala Leu Pro Asp Ala Val Thr Arg Arg
            20                  25                  30

Leu Thr Arg Leu Leu Leu Ala Gln Arg Leu Arg Leu Gly Tyr Leu Pro
        35                  40                  45

Ser Ser Ser Ser Ser Ala Pro Leu His Leu His His Leu Leu Leu Phe
    50                  55                  60

Ala His Ala Leu Glu Glu Met Pro Ile Ala Ile Glu Thr Glu Lys Ala
65                  70                  75                  80

Lys Xaa Gln His Tyr Glu Leu Pro Thr Thr Phe Phe Lys Leu Val Leu
                85                  90                  95

Gly Arg Asn Leu Lys Tyr Ser Ser Cys Tyr Phe Pro Asp Glu Ser Ser
                100                 105                 110

Thr Leu Glu Asp Ala Xaa Val
        115
```

```
<210> SEQ ID NO 7
<211> LENGTH: 936
<212> TYPE: DNA
<213> ORGANISM: Glycine max

<400> SEQUENCE: 7
gcacgagggg aagagcccctt tgtggttgtg gttgtgggta ggtgctgctg ctgcttccat    60
tcctattctt acagtgaagg ttcaatggaa gggacaatgc agcttgcata cgagactgtt   120
gtgaagctca tgctggctgc actcgaacgc aacgtgctcc tgacgtcat caccaggaga    180 ctcacgcgct gctgttggc tactcgcctt cgctctgctt acaaaccctc ctcccaactt    240
caactctccg atcctctcta cttcgcgcat tcattacaag atgcccat agcaatcaac     300 actgacaagc taagtctca acattatgaa ttaccaaccg ctttcttcaa gctcgtcctc    360
ggaaacaatc tcaaatacag ctgttgttat ttctcttctg cctcaatgac gctggatgat    420
gctgaagaag caatgttgaa actgtactgt gagagatcaa acctgaaaga tggtcataca    480
gtgcttgatg tgggatgcgg ttggggatcg ttggctctat acattgccaa gaattacact   540
aactgtaggg ttacaggaat ctgcaattcc acaactcaaa aggcttatat tgaggagaag   600
```

```
tgtagggatc ttcagctgca aaatttgaat attatagttg ctgatattag cacatttgaa    660
atggagactt cttatgacag aatattttcc atagaaatgt ttgagcatat gaagaactat    720
aaagatcttc tgaagaagat atccaaatgg atgaaagagg atagccttt atttgttcat     780 tacttctgcc acaaagcatt tgcctaccac tttgaggaca aaaatgaaga tgactggatt    840
acaagatact tctttactgg aggaactatg ccttcggcaa atctacttct ttattccaag    900
atgatgttac tgtcacaacc attgggctac taatgg                              936
```

<210> SEQ ID NO 8
<211> LENGTH: 298
<212> TYPE: PRT
<213> ORGANISM: Glycine max

<400> SEQUENCE: 8

```
Ala Arg Gly Glu Glu Pro Phe Val Val Val Gly Arg Cys Cys
1               5                   10                  15

Cys Cys Phe His Ser Tyr Ser Tyr Ser Glu Gly Ser Met Glu Gly Thr
            20                  25                  30

Met Gln Leu Ala Tyr Glu Thr Val Val Lys Leu Met Leu Ala Ala Leu
        35                  40                  45

Glu Arg Asn Val Leu Pro Asp Val Ile Thr Arg Arg Leu Thr Arg Leu
    50                  55                  60

Leu Leu Ala Thr Arg Leu Arg Ser Ala Tyr Lys Pro Ser Ser Gln Leu
65                  70                  75                  80

Gln Leu Ser Asp Leu Leu Tyr Phe Ala His Ser Leu Gln Glu Met Pro
                85                  90                  95

Ile Ala Ile Asn Thr Asp Lys Pro Lys Ser Gln His Tyr Glu Leu Pro
            100                 105                 110

Thr Ala Phe Phe Lys Leu Val Leu Gly Asn Asn Leu Lys Tyr Ser Cys
        115                 120                 125

Cys Tyr Phe Ser Ser Ala Ser Met Thr Leu Asp Asp Ala Glu Glu Ala
    130                 135                 140

Met Leu Lys Leu Tyr Cys Glu Arg Ser Asn Leu Lys Asp Gly His Thr
145                 150                 155                 160

Val Leu Asp Val Gly Cys Gly Trp Gly Ser Leu Ala Leu Tyr Ile Ala
                165                 170                 175

Lys Asn Tyr Thr Asn Cys Arg Val Thr Gly Ile Cys Asn Ser Thr Thr
            180                 185                 190

Gln Lys Ala Tyr Ile Glu Glu Lys Cys Arg Asp Leu Gln Leu Gln Asn
        195                 200                 205

Leu Asn Ile Ile Val Ala Asp Ile Ser Thr Phe Glu Met Glu Thr Ser
    210                 215                 220

Tyr Asp Arg Ile Phe Ser Ile Glu Met Phe Glu His Met Lys Asn Tyr
225                 230                 235                 240

Lys Asp Leu Leu Lys Lys Ile Ser Lys Trp Met Lys Glu Asp Ser Leu
                245                 250                 255

Leu Phe Val His Tyr Phe Cys His Lys Ala Phe Ala Tyr His Phe Glu
            260                 265                 270

Asp Lys Asn Glu Asp Asp Trp Ile Thr Arg Tyr Phe Phe Thr Gly Gly
        275                 280                 285

Thr Met Pro Ser Ala Asn Leu Leu Leu Tyr
    290                 295
```

<210> SEQ ID NO 9

-continued

```
<211> LENGTH: 722
<212> TYPE: DNA
<213> ORGANISM: Triticum aestivum
<220> FEATURE:
<221> NAME/KEY: unsure
<222> LOCATION: (41)
<223> OTHER INFORMATION: n = A, C, G, or T
<220> FEATURE:
<221> NAME/KEY: unsure
<222> LOCATION: (677)
<223> OTHER INFORMATION: n = A, C, G, or T
<220> FEATURE:
<221> NAME/KEY: unsure
<222> LOCATION: (700)
<223> OTHER INFORMATION: n = A, C, G, or T
<220> FEATURE:
<221> NAME/KEY: unsure
<222> LOCATION: (703)
<223> OTHER INFORMATION: n = A, C, G, or T
<220> FEATURE:
<221> NAME/KEY: unsure
<222> LOCATION: (710)
<223> OTHER INFORMATION: n = A, C, G, or T

<400> SEQUENCE: 9
gcagcccggc ccaaattcct ggcagcagca gcagcagcag nagccggcgc cgggagagga      60
gcgagcaaga atggcggcgg cggccgtggc agcgcgggcg tacgaggcgg cggcgcggtc     120
cgcgctggcg gcgctggagc gcaacctcct gcccgacgcg gtcacccggc ggctcacgcg     180
cttcctgctc gcgcagcgcc tccgcctcgg cacgctcccc tccgcgccgc tccagctgca     240
ggacctcctc ctcttcgccc actcacttga aggcatgccc attgccattg aaacggacac     300
agctaaaacc cagcactacg agctgccgac cacattcttc aagctagtgc tcggaaaaaa     360
cctcaaatac agctcatgtt acttccccga tgattcaagc accctagaag atgccgaggt     420
tgcaatgttg gagttgtact gtgagagggc gcagctgcaa gatggccaaa gcattctcga     480
tgttggatgt ggatggggat ccctctctgt atacatagca aagaaatata ggaactgcaa     540
tatcacaggg atatgcaact caacaactca aagggttttt atagaaaagc agtgtaggga     600
aaatgagcta tcaaatgttg agataattgt tgcagacatc agcaagtttg agatggacgt     660
tcttttgcag gatatancat agagatgttt gacacatgan aantacaggn aattcttaga     720
ag                                                                   722

<210> SEQ ID NO 10
<211> LENGTH: 195
<212> TYPE: PRT
<213> ORGANISM: Triticum aestivum

<400> SEQUENCE: 10

Met Ala Ala Ala Ala Val Ala Ala Arg Ala Tyr Glu Ala Ala Ala Arg
  1               5                  10                  15

Ser Ala Leu Ala Ala Leu Glu Arg Asn Leu Leu Pro Asp Ala Val Thr
                 20                  25                  30

Arg Arg Leu Thr Arg Phe Leu Leu Ala Gln Arg Leu Arg Leu Gly Thr
             35                  40                  45

Leu Pro Ser Ala Pro Leu Gln Leu Gln Asp Leu Leu Leu Phe Ala His
         50                  55                  60

Ser Leu Glu Gly Met Pro Ile Ala Ile Glu Thr Asp Thr Ala Lys Thr
 65                  70                  75                  80

Gln His Tyr Glu Leu Pro Thr Thr Phe Phe Lys Leu Val Leu Gly Lys
                 85                  90                  95

Asn Leu Lys Tyr Ser Ser Cys Tyr Phe Pro Asp Asp Ser Ser Thr Leu
```

```
                    100                 105                 110
Glu Asp Ala Glu Val Ala Met Leu Glu Leu Tyr Cys Glu Arg Ala Gln
            115                 120                 125

Leu Gln Asp Gly Gln Ser Ile Leu Asp Val Gly Cys Gly Trp Gly Ser
        130                 135                 140

Leu Ser Val Tyr Ile Ala Lys Lys Tyr Arg Asn Cys Asn Ile Thr Gly
145                 150                 155                 160

Ile Cys Asn Ser Thr Thr Gln Lys Gly Phe Ile Glu Lys Gln Cys Arg
                165                 170                 175

Glu Asn Glu Leu Ser Asn Val Glu Ile Ile Val Ala Asp Ile Ser Lys
            180                 185                 190

Phe Glu Met
        195

<210> SEQ ID NO 11
<211> LENGTH: 382
<212> TYPE: PRT
<213> ORGANISM: Escherichia coli

<400> SEQUENCE: 11

Met Ser Ser Ser Cys Ile Glu Glu Val Ser Val Pro Asp Asp Asn Trp
 1               5                  10                  15

Tyr Arg Ile Ala Asn Glu Leu Leu Ser Arg Ala Gly Ile Ala Ile Asn
            20                  25                  30

Gly Ser Ala Pro Ala Asp Ile Arg Val Lys Asn Pro Asp Phe Phe Lys
        35                  40                  45

Arg Val Leu Gln Glu Gly Ser Leu Gly Leu Gly Glu Ser Tyr Met Asp
     50                  55                  60

Gly Trp Trp Glu Cys Asp Arg Leu Asp Met Phe Phe Ser Lys Val Leu
 65                  70                  75                  80

Arg Ala Gly Leu Glu Asn Gln Leu Pro His His Phe Lys Asp Thr Leu
                85                  90                  95

Arg Ile Ala Gly Ala Arg Leu Phe Asn Leu Gln Ser Lys Lys Arg Ala
            100                 105                 110

Trp Ile Val Gly Lys Glu His Tyr Asp Leu Gly Asn Asp Leu Phe Ser
        115                 120                 125

Arg Met Leu Asp Pro Phe Met Gln Tyr Ser Cys Ala Tyr Trp Lys Asp
    130                 135                 140

Ala Asp Asn Leu Glu Ser Ala Gln Gln Ala Lys Leu Lys Met Ile Cys
145                 150                 155                 160

Glu Lys Leu Gln Leu Lys Pro Gly Met Arg Val Leu Asp Ile Gly Cys
                165                 170                 175

Gly Trp Gly Gly Leu Ala His Tyr Met Ala Ser Asn Tyr Asp Val Ser
            180                 185                 190

Val Val Gly Val Thr Ile Ser Ala Glu Gln Gln Lys Met Ala Gln Glu
        195                 200                 205

Arg Cys Glu Gly Leu Asp Val Thr Ile Leu Leu Gln Asp Tyr Arg Asp
    210                 215                 220

Leu Asn Asp Gln Phe Asp Arg Ile Val Ser Val Gly Met Phe Glu His
225                 230                 235                 240

Val Gly Pro Lys Asn Tyr Asp Thr Tyr Phe Ala Val Val Asp Arg Asn
                245                 250                 255

Leu Lys Pro Glu Gly Ile Phe Leu Leu His Thr Ile Gly Ser Lys Lys
            260                 265                 270
```

-continued

```
Thr Asp Leu Asn Val Asp Pro Trp Ile Asn Lys Tyr Ile Phe Pro Asn
        275                 280                 285

Gly Cys Leu Pro Ser Val Arg Gln Ile Ala Gln Ser Ser Glu Pro His
        290                 295                 300

Phe Val Met Glu Asp Trp His Asn Phe Gly Ala Asp Tyr Asp Thr Thr
305                     310                 315                 320

Leu Met Ala Trp Tyr Glu Arg Phe Leu Ala Ala Trp Pro Glu Ile Ala
                325                 330                 335

Asp Asn Tyr Ser Glu Arg Phe Lys Arg Met Phe Thr Tyr Tyr Leu Asn
            340                 345                 350

Ala Cys Ala Gly Ala Phe Arg Ala Arg Asp Ile Gln Leu Trp Gln Val
        355                 360                 365

Val Phe Ser Arg Gly Val Glu Asn Gly Leu Arg Val Ala Arg
        370                 375                 380
```